(12) United States Patent
Hourmand et al.

(10) Patent No.: US 9,205,200 B2
(45) Date of Patent: *Dec. 8, 2015

(54) FINGER GUARD FOR AN INJECTION DEVICE

(75) Inventors: Yannick Hourmand, Haslingfield (GB); Simon Francis Brereton, Cambridge (GB); Thomas Kemp, Ashwell (GB); Rosie Burnell, Cambridge (GB); Matthew Ekman, Macclesfield (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/877,496

(22) PCT Filed: Oct. 6, 2011

(86) PCT No.: PCT/EP2011/067503
§ 371 (c)(1),
(2), (4) Date: Aug. 19, 2013

(87) PCT Pub. No.: WO2012/045840
PCT Pub. Date: Apr. 12, 2012

(65) Prior Publication Data
US 2013/0317449 A1 Nov. 28, 2013

Related U.S. Application Data

(60) Provisional application No. 61/432,256, filed on Jan. 13, 2011.

(30) Foreign Application Priority Data

Oct. 8, 2010 (EP) .................................... 10187009

(51) Int. Cl.
*A61M 5/32* (2006.01)
*A61M 5/20* (2006.01)
*A61M 5/315* (2006.01)
*A61M 5/46* (2006.01)

(52) U.S. Cl.
CPC ........... *A61M 5/3213* (2013.01); *A61M 5/2033* (2013.01); *A61M 5/31501* (2013.01); *A61M5/31595* (2013.01); *A61M 5/326* (2013.01); *A61M 5/3221* (2013.01); *A61M 5/3202* (2013.01); *A61M 5/3204* (2013.01); *A61M 5/46* (2013.01); *A61M 2005/206* (2013.01)

(58) Field of Classification Search
CPC ... A61M 5/20; A61M 5/2033; A61M 5/3157; A61M 5/3202; A61M 5/3204; A61M 5/3213; A61M 5/3221; A61M 5/3257; A61M 5/3287; A61M 2005/206; A61M 2005/3247; A61M 2205/581; A61M 2205/582
USPC .................. 604/197, 198, 134–138, 156, 157
See application file for complete search history.

(56) References Cited

U.S. PATENT DOCUMENTS 4,795,432 A    1/1989   Karczmer
6,371,939 B2 * 4/2002   Bergens et al. ............... 604/156
(Continued)

FOREIGN PATENT DOCUMENTS

JP      2001-259034      9/2001

OTHER PUBLICATIONS

International Search Report for Int. App. No. PCT/EP2011/067503, completed Jan. 11, 2012.

*Primary Examiner* — Andrew Gilbert
(74) *Attorney, Agent, or Firm* — Fish & Richardson P.C.

(57) ABSTRACT

The invention refers to a finger guard for an injection device with a hollow injection needle arranged to be hidden inside a component with an orifice prior to use and to be advanced relative to the component through the orifice for inserting it into an injection site, the finger guard comprising a spring wire attached to the component and comprising an arcuate transversal section biased in a manner to flex inwards so as to essentially obstruct the orifice for finger access when released but staying enough off-centre to allow the needle to advance through the orifice without touching the spring wire.

15 Claims, 11 Drawing Sheets

(56) References Cited

U.S. PATENT DOCUMENTS

| | | | |
|---|---|---|---|
| 7,635,350 B2* | 12/2009 | Scherer | 604/136 |
| 8,876,768 B2* | 11/2014 | Hourmand et al. | 604/136 |
| 2002/0095120 A1 | 7/2002 | Larsen et al. | |
| 2004/0111063 A1 | 6/2004 | Botich et al. | |
| 2008/0255526 A1 | 10/2008 | Bosse et al. | |
| 2010/0036318 A1* | 2/2010 | Raday et al. | 604/134 |
| 2013/0035645 A1* | 2/2013 | Bicknell et al. | 604/198 |

* cited by examiner

FINGER GUARD FOR AN INJECTION DEVICE

CROSS REFERENCE TO RELATED APPLICATIONS

The present application is a U.S. National Phase Application pursuant to 35 U.S.C. §371 of International Application No. PCT/EP2011/067503 filed Oct. 6, 2011, which claims priority to European Patent Application No. 10187009.5 filed Oct. 8, 2010 and U.S. Provisional Patent Application No. 61/432,256 filed Jan. 13, 2011. The entire disclosure contents of these applications are herewith incorporated by reference into the present application.

TECHNICAL FIELD

The invention relates to a finger guard for an injection device for preventing finger access to an injection needle.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

US 2002/0095120 A1 discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, torsion stored in the tension spring is released and the injection needle is automatically retracted back to its original storage position.

Usually the injection needle is equipped with a protective needle shield for keeping the needle sterile and preventing it from being mechanically damaged. The protective needle shield is attached to the needle when the syringe is assembled. In order to prepare for an injection the user has to remove the protective needle shield. During and after removal the risk for needle stick injuries is more or less increased depending on the design of the syringe or the injection device.

SUMMARY

It is an object of the present invention to provide a finger guard for protecting a user's fingers from needle-stick injuries.

The object is achieved by a finger guard according to claim 1.

Preferred embodiments of the invention are given in the dependent claims.

In the context of this specification the term proximal refers to the direction pointing towards the patient during an injection while the term distal refers to the opposite direction pointing away from the patient.

A finger guard according to the invention is intended to be applied in an injection device with a hollow injection needle arranged to be hidden in a component with an orifice prior to use and to be advanced relative to the component through the orifice for inserting it into an injection site. The finger guard comprises a spring wire attached to the component and comprising an arcuate transversal section biased in a manner to flex inwards so as to essentially obstruct the orifice for finger access when released but staying enough off-centre to allow the needle to advance through the orifice without touching the spring wire. The spring wire allows the needle to be as near as possible to the orifice prior to use thus reducing travel of the syringe and the overall length of the auto-injector but still preventing needle stick injuries.

Usually the hollow needle is equipped with a protective needle shield for keeping the needle sterile and preventing it from being mechanically damaged.

The finger guard may protect an orifice wide enough for the protective needle shield and a remover for the protective needle shield, e.g. parts of a cap of the injection device. Without a finger guard such a wide orifice may become accessible for at least a child's finger after removal of the protective needle shield. With the finger guard the orifice is roughly bisected thus preventing finger access.

A notch may be arranged in a proximal face of the component near the orifice for catching the arcuate transversal section when it is released and allowed to flex inwards. This prevents the spring wire from being easily pushed aside by the user and hence increases needle safety. Furthermore, the cap is kept from being reattached to the auto-injector after removal thus preventing damage and blunting to the needle before injection.

The cap may comprise an inner cylinder arranged to extend into the orifice for removing the protective needle shield. The inner cylinder may be arranged for keeping the arcuate transversal section from flexing inwards when the cap is attached to the auto-injector.

The component where the finger guard is attached may be arranged as a chassis of the injection device or as a tubular shroud arranged to be advanced for covering the needle and to be retracted for exposing the needle.

The finger guard may be applied in all kinds of injection devices for administering a dose of a liquid medicament.

In one embodiment the finger guard is applied in an auto-injector.

The auto-injector for administering a dose of a liquid medicament may comprise:
- the chassis arranged to contain a syringe with the hollow needle and a stopper for sealing the syringe and displacing the medicament, wherein the syringe is slidably arranged with respect to the chassis,
- drive means capable of, upon activation:
- pushing the needle from a covered position inside the chassis into an advanced position through the orifice and past the proximal end,
- operating the syringe to supply the dose of medicament, and
- retracting the syringe with the needle into the covered position after delivering the medicament,
- activating means arranged to lock the drive means prior to manual operation and capable of, upon manual operation, releasing the drive means for injection.

Conventional auto-injectors achieve needle safety by starting with the needle held some distance back within the body of the device. Upon actuation the needle moves forward by a distance that is the sum of the hiding distance and the required injection depth. By using the aforementioned finger guard, the hiding distance may be safely reduced. Thus the auto-injector may be made shorter, more portable and attractive to users.

The drive means may be a drive spring in the shape of a compression spring arranged to be grounded at a distal end in the chassis for advancing the needle and for injecting the dose of medicament via a plunger. The drive spring is arranged to have its ground in the chassis switched to its proximal end for retracting the syringe.

The single compression spring is used for inserting the needle, fully emptying the syringe and retracting the syringe and needle to a safe position after injection. Thus a second spring for withdrawing the syringe and needle, which is a motion with an opposite sense compared to advancing the syringe and injecting the dose, is not required. While the distal end of the compression spring is grounded the proximal end moves the syringe forward for inserting the needle and carries on to the injection by pushing on the stopper. When the injection is at least nearly finished the compression spring bottoms out at its proximal end, resulting in the proximal end being grounded in the chassis. The distal end of the compression spring may now be released from its ground in the chassis. The compression spring is now pulling the syringe in the opposite direction.

The use of just one compression spring reduces the amount of metal needed and thus consequently reduces weight and manufacturing costs.

A retraction sleeve may be axially movable arranged around the syringe. The retraction sleeve is fixable to the chassis in a maximum proximal position for providing ground at the distal end of the drive spring. The retraction sleeve is arranged to take the syringe with it when released and translated in distal direction. The compression spring is wrapped over the retraction sleeve with its distal end, bearing against a thrust face on the refraction sleeve and with its proximal end bearing against a thrust collar arranged to be coupled to the plunger for joint axial translation for advancing the needle and for injecting the dose of medicament. The thrust collar is arranged to be decoupled from the plunger for retraction.

Due to the drive spring wrapped over the plunger and the retraction sleeve its length is not added to the overall length of the auto-injector. Consequently, the auto-injector according to the invention can be made shorter.

In one embodiment of the invention the activating means is arranged as a trigger button in the shape of a wrap-over sleeve button arranged over the distal end of the auto-injector. The trigger button extends at least almost over the whole length of the auto-injector. The trigger button is arranged to release the drive spring upon translation in proximal direction. The trigger button is arranged to release the drive spring upon translation in proximal direction. In order to trigger an injection the auto-injector has to be pressed against an injection site, e.g. a patient's skin. A user, e.g. the patient or a caregiver, grabs the wrap-over sleeve button with their whole hand and pushes against the injection site. Consequently, the trigger button translates in proximal direction and releases the drive spring for starting the injection cycle. This embodiment is particularly well suited for people with dexterity problems since triggering does not require operation of small buttons by single fingers. Instead, the whole hand is used.

An interlock sleeve may be telescoped with the proximal end of the chassis and with the trigger button. The interlock sleeve is translatable in longitudinal direction between a proximal position relative to the trigger button and a distal position relative to the chassis and biased towards the proximal position, e. g. by an interlock spring. The interlock sleeve is arranged to release the retraction sleeve when in the proximal position and with the trigger button translated in proximal direction, i.e. when the injection has been triggered by actuating the trigger button followed by removal of the auto-injector from the injection site and consequent translation of the interlock sleeve into a final proximal position. The interlock sleeve is arranged to block the translation of the retraction sleeve otherwise, so the syringe is only retracted if an injection cycle has been started before and if the user removes the auto-injector from the injection site. As the proximal position of the interlock sleeve is limited by the trigger button or a component attached to the trigger button the final proximal position of the interlock sleeve after actuation of the trigger button is further advanced with respect to the chassis as an initial proximal position before actuation of the trigger button.

In order to hold or release the retraction sleeve the interlock sleeve may comprise at least one leg arranged distally. At least one third resilient clip is arranged on the proximal end of the retraction sleeve, wherein a respective protrusion for each third resilient clip is arranged on the chassis. The third resilient clip and/or the protrusion exhibit a ramp for flexing the third resilient clip away from the protrusion for disengaging them under load of the drive spring thus releasing the retraction sleeve. The leg is arranged to allow this disengagement only when the interlock sleeve is in the final proximal position with the trigger button translated in proximal direction. Otherwise the leg is arranged to support the third resilient clip in a manner to prevent it from flexing away from the protrusion thus keeping them engaged and blocking the retraction sleeve in a manner to prevent it from translating.

The retraction sleeve may exhibit at least one moving shutter and the chassis may comprises a fixed shutter, the shutters forming a shuttering mechanism for controlling translation of the plunger. The moving shutter and the fixed shutter respectively comprise a number of regularly spaced castellation. The castellations of the moving shutter are out of phase with the castellations of the fixed shutter when the retraction sleeve is fixed in the maximum proximal position thus creating a surface of alternating castellations of both shutters for a respective first clip to travel along. The first clip is connected to the plunger and arranged to keep the thrust collar coupled to the plunger when being held on the level of that surface. On translation of the retraction sleeve in distal direction the moving shutter gets in phase with the fixed shutter in a manner to regularly interrupting the surface by gaps between consecutive castellation allowing the first clip to be flexed inwards into the gaps or proximally behind the most proximal castellations. The first clip is flexed inwards by at least one ramp on the first clip and/or on the thrust collar under load of the drive spring. By the first clip flexing inwards the thrust collar is decoupled from the plunger. Consequently the plunger is no longer pushed in proximal direction and does not prevent retraction of the syringe and needle, so they can be retracted along with the plunger.

A decoupling sleeve may be arranged around the retraction sleeve inside the drive spring. The decoupling sleeve is attached to the plunger at a distal end. The decoupling sleeve may therefore be considered part of the plunger. However, having two different parts is preferred for assembly purposes. Prior to manual operation of the activating means the thrust collar is coupled through the first clip and the decoupling sleeve to the retraction sleeve. The activating means is arranged to prevent decoupling of the decoupling sleeve from the retraction sleeve prior to actuation and to allow decoupling on actuation. Since the retraction sleeve is coupled to the chassis in this situation the injection cannot start before actuation of the activating means.

For interacting with the activating means, e.g. the trigger button, the decoupling sleeve may exhibit a resilient arm protruding in distal direction, the resilient arm having a wedge arranged to be held between a ramp on the retraction sleeve and a bar protruding in proximal direction from a distal end face of the trigger button prior to actuation of the trigger button. Upon actuation of the trigger button the bar is translated so as to allow the wedge to be flexed into a recess in the bar by the ramp on the retraction sleeve under load of the drive spring.

The trigger button does not have to be pushed against the force of the drive spring thus allowing for a drive spring with a high spring force suitably for thin needles and highly viscous medicaments without the user having to exert too high an activation force.

Preferably a cap is provided at the proximal end of the auto-injector. A sheet metal clip is attached to the cap for joint axial movement and independent rotation. The sheet metal clip is arranged to extend through the orifice into the chassis when the cap is attached to the auto-injector. The sheet metal clip may comprise at least two barbs snapped into a circumferential notch or behind a shoulder of the protective needle shield. This allows for automatically engaging the sheet metal clip with the protective needle shield during assembly. When the cap is removed from the auto-injector in preparation of an injection the protective needle shield is reliably removed without exposing the user to too high a risk to injure themselves.

The cap may be attachable to the auto-injector by a screw connection. This allows for a low force removal of the protective needle shield.

The interlock sleeve may be telescoped in the sleeve trigger button or in a head part attached to the proximal end of the sleeve trigger button. A force required to translate the interlock sleeve in distal direction is preferably lower than a force required to translate the trigger button in proximal direction thus providing a two stage operation with a step in the force felt by the user when pushing the auto-injector against the injection site.

A decoupling carrier may be slidably arranged in the refraction sleeve and coupled to the syringe for joint axial translation. The decoupling carrier comprises at least one second resilient clip engageable in a detent in or behind a shoulder on the plunger in a manner to lock the decoupling carrier to the plunger for joint axial translation. The retraction sleeve is arranged for outwardly supporting the second resilient clip prior to the syringe reaching an injection depth during needle insertion. A respective aperture for each second resilient clip is arranged in the retraction sleeve allowing the second resilient clip to be flexed outwards and disengage from the detent upon the syringe reaching the injection depth thus coupling the plunger to the stopper. Consequently, a so called wet injection is avoided, i.e. the liquid medicament is not leaking out of the hollow needle before the needle is inserted.

The sleeve trigger button may have at least one viewing window for inspecting the syringe.

The auto-injector may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a proteine, antibodies and complex carbohydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figures 1A, 1B:
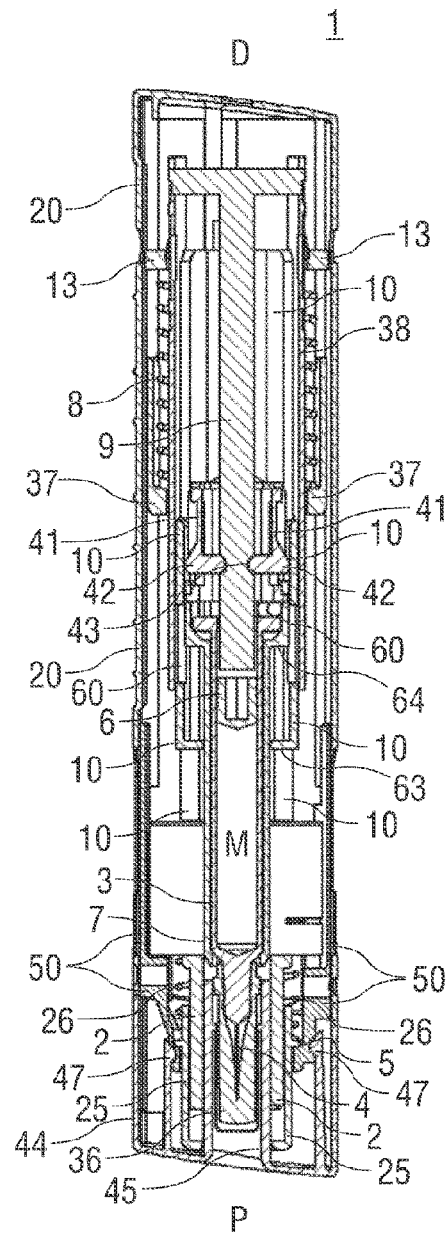
FIG. 1 are longitudinal sections of an auto-injector in an as delivered, initial state with a cap.

FIG. 1 shows two longitudinal sections in different section planes of an auto-injector 1, the different section planes approximately 90° rotated to each other. The auto-injector 1 comprises a chassis 2. A syringe 3, e.g. a Hypak syringe, with a hollow needle 4 is arranged in a proximal part of the auto-injector 1. When the auto-injector 1 or the syringe 3 is assembled a protective needle shield 36 is attached to the needle 4. A stopper 6 is arranged for sealing the syringe 3 distally and for displacing a liquid medicament M through the hollow needle 4. The syringe 3 is held in a tubular syringe carrier 7 and supported at its proximal end therein. The syringe carrier 7 is slidably arranged in the chassis 2. A single drive spring 8 in the shape of a compression spring is arranged in a distal part of the auto-injector 1.

The drive spring 8 is loaded between a retraction sleeve 10 and a thrust collar 37. A plunger 9 for forwarding the spring force of the drive spring 8 to the syringe 3 and/or the stopper 6 is mechanically linked to a decoupling sleeve 38 at a distal end of the plunger 9. The plunger 9 and the decoupling sleeve 38 are slidable in longitudinal direction. The drive spring 8 is wrapped over the decoupling sleeve 38. The thrust collar 37 is coupled with the decoupling sleeve 38 for joint axial translation by a pair of first clips 39 arranged proximally at the decoupling sleeve 38. Inside the thrust collar 37 and the decoupling sleeve 38 the retraction sleeve 10 is slidably arranged. The retraction sleeve 10 comprises a thrust face 13 extending through apertures in the decoupling sleeve 38 so as to bear against the distal end of the drive spring 8. Inside the refraction sleeve 10 a decoupling carrier 41 is slidably arranged. The decoupling carrier 41 is coupled to the syringe carrier 7 for joint axial translation. The decoupling carrier 41 comprises two resilient second clips 42 engageable in a detent 43 in the plunger 9 in a manner to lock the decoupling carrier 41 to the plunger 9 for joint axial translation. At least in an initial state prior to actuation the second resilient clips 42 are engaged in the detent 43 and outwardly supported by the retraction sleeve 10 and thus prevented from flexing outwards and disengaging from the detent 43.

A trigger button 20 is arranged in the shape of a wrap-over sleeve button over the distal end D of the auto-injector 1 extending almost over the whole length of the auto-injector 1. A head part 50 is attached at the proximal end P of the trigger button 20. The trigger button 20 and the head part 50 are slidable in longitudinal direction with respect to the chassis 2.

A skin interlock sleeve 25 is arranged at the proximal end P and telescoped with the chassis 2. The interlock sleeve 25 is telescoped in the head part 50 of the wrap-over trigger button 20. An interlock spring 26 for biasing the interlock sleeve 25 in proximal direction P against the chassis 2 is arranged inside the head part 50. The head part 50 provides a first abutment 5 limiting translation of the interlock sleeve 25 in proximal direction P.

Figure 2:
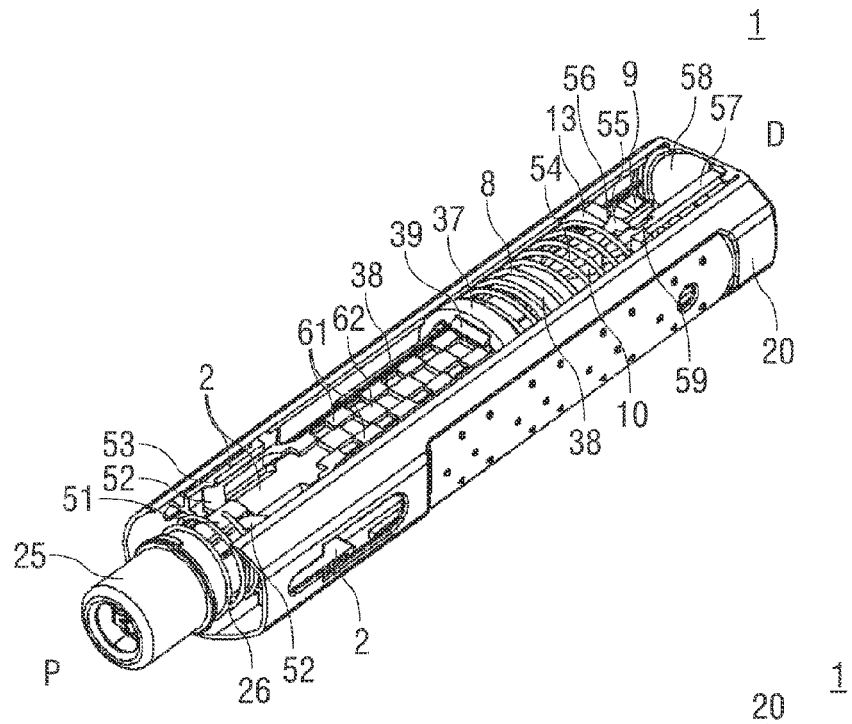
FIG. 2 is an isometric sectional view of the auto-injector.
Figure 3:
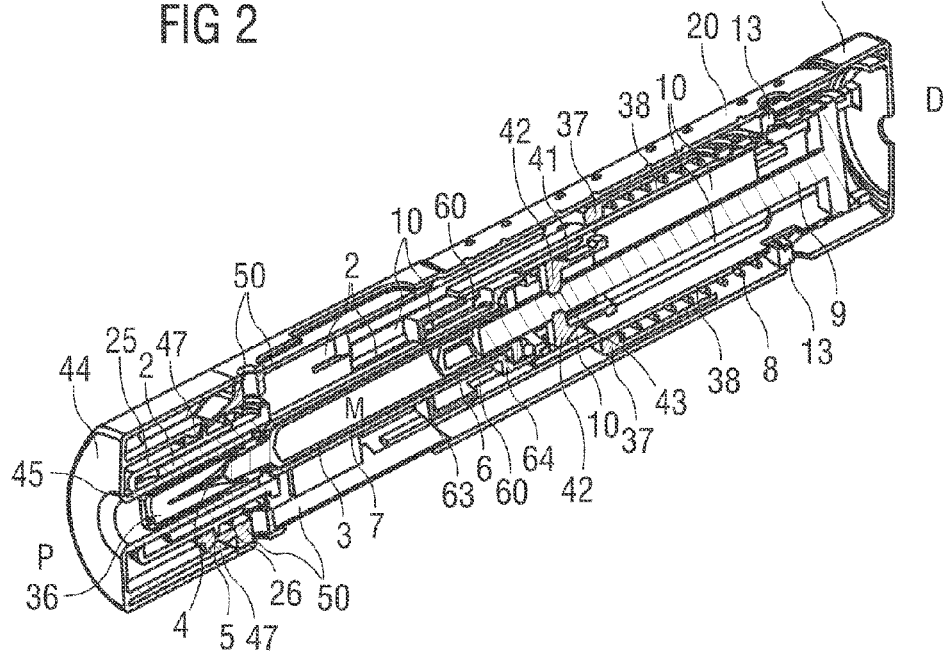
FIG. 3 is another isometric sectional view of the auto-injector.

FIG. 2 is an isometric sectional view of the auto-injector 1 without the cap 44 and the head part 50 for better recognisability of interior parts.

The skin interlock sleeve 25 comprises two legs 51 arranged distally (see FIG. 2, only one leg shown, the other one is on the opposite side). In the initial state the legs 51 are arranged between two third resilient clips 52 on the proximal end of the retraction sleeve 10 thus keeping them from flexing inwards. Outwardly, the third clips 52 are held behind protrusions 53 (one of them illustrated, the other one masked in FIG. 2) in the chassis 2 in a manner to prevent translation of the retraction sleeve 10 in distal direction D. Thus, the distal end of the compression spring 8 is grounded in the chassis 2. The retraction sleeve 10 exhibits a number of moving shutters 61 and the chassis 2 comprises a fixed shutter 62. The moving shutter 61 and the fixed shutter 62 respectively comprise a number of regularly spaced castellations. In the initial state the castellations of the moving shutters 61 are out of phase with the castellations of the fixed shutter 62 (cf. FIGS. 1 and 2) thus creating a surface of alternating castellations of both shutters 61, 62 for the first clip 39 to travel along without allowing the first clip 39 to flex inwards. If the retraction sleeve 10 is translated so as to bring the moving shutter 61 in phase with the fixed shutter 62 (not illustrated) the surface is regularly interrupted by gaps allowing the first clip 39 to flex inwards by ramps on the first clip 39 interacting with ramps on the thrust collar 37 under load of the drive spring 8 thus decoupling the thrust collar 37 from the decoupling sleeve 38.

Initially the drive spring 8 is grounded to the thrust face 13 of the retraction sleeve 10 and bears against the thrust collar 37. The retraction sleeve 10 is prevented from translating in distal direction D because of the engagement of the third clips 52 to the chassis 2 and the legs 51. The thrust collar 37 is kept from translating in proximal direction P by engagement to the retraction sleeve 10 through the first clips 39 and the decoupling sleeve 38. The decoupling sleeve 38 exhibits a resilient arm 54 protruding in distal direction D with a wedge 55 held between a ramp 56 on the retraction sleeve 10 and a bar 57 protruding in proximal direction P from a distal end face 58 of the trigger button 20 (see FIG. 2). In the initial position under load of the drive spring 8 the ramp 56 tries to flex the wedge 55 aside but is kept from doing so by the bar 57 supporting the wedge 55 from opposite the ramp 56.

Figure 7:
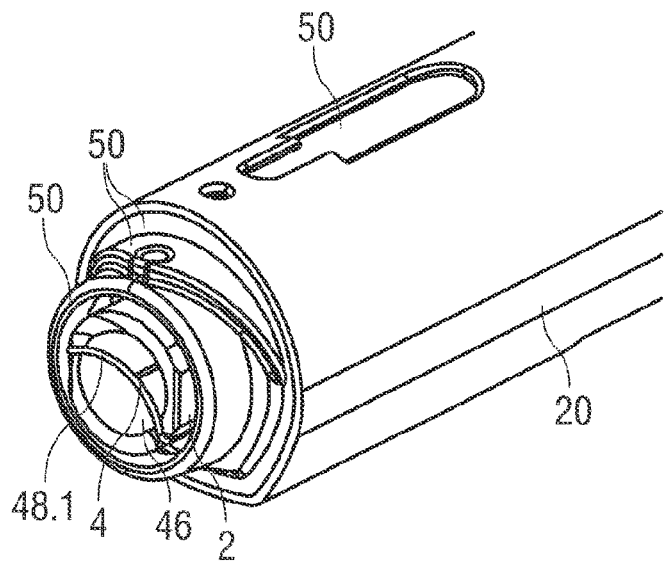
FIG. 7 is an isometric view of the proximal end of the auto-injector after removal of the cap with an activated finger guard.
Figure 8:
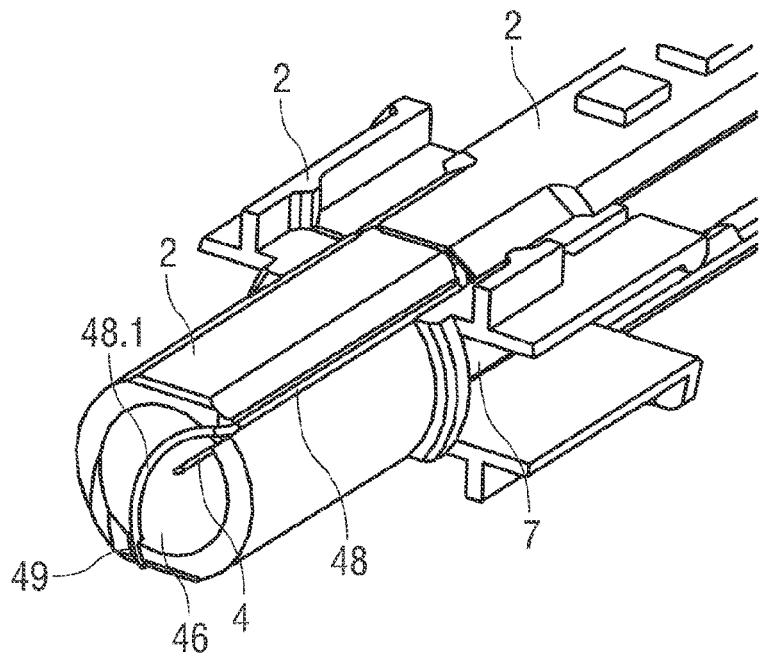
FIG. 8 is an isometric view of a chassis of the auto-injector with the activated finger guard.

A cap 44 is arrangeable at the proximal end of the auto-injector 1. The cap 44 comprises an inner cylinder 45 arranged to extend into an orifice 46 (see FIGS. 6, 7, 8) in the proximal end of the chassis 2. The orifice 46 needs to be considerably wider than the needle 4 because of the space required for the protective needle shield 36 and the inner cylinder 45. In an initial state prior to use the inner cylinder 45 grips the protective needle shield 36 which is arranged on the needle 4.

Figure 5:
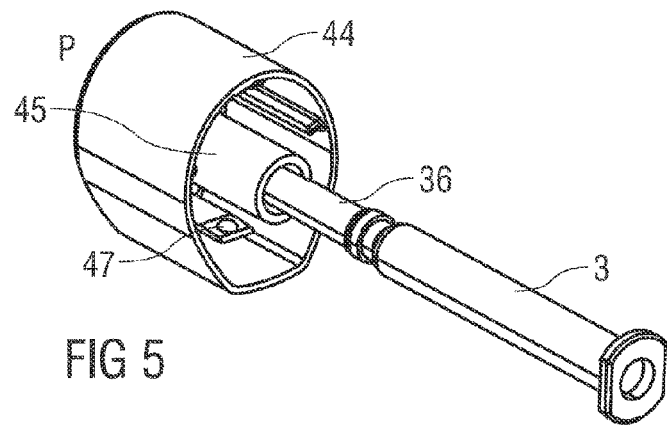
FIG. 5 is an isometric view of the cap with a protective needle shield and a syringe.

In order to prepare for an injection the cap 44 has to be removed. FIG. 5 is an isometric view of the cap 44 with the protective needle shield 36 and the syringe 3. On removal of the cap 44 the protective needle shield 36 is removed, too. The force required to pull the protective needle shield 36 off the syringe 3 is relatively high. In order to avoid the syringe 3 being pulled in proximal direction P during removal of the protective needle shield 36 the syringe 3 has to be held firmly in position. This is achieved by the syringe 3 being supported at its proximal end in the syringe carrier 7, the syringe carrier 7 being coupled to the decoupling carrier 41, the decoupling carrier 41 being engaged to the plunger 9, the plunger 9 attached to the decoupling sleeve 38, the decoupling sleeve 38 prevented from advancing by the wedge 55 held between the ramp 56 on the retraction sleeve 10 and the bar 57 and by the retraction sleeve 10.

Figure 4:
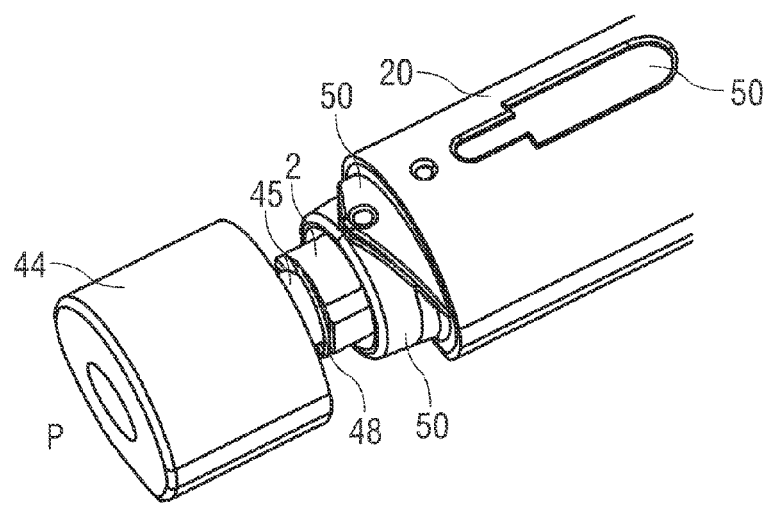
FIG. 4 is an isometric view of a proximal end of the auto-injector during removal of a cap.
Figure 6:
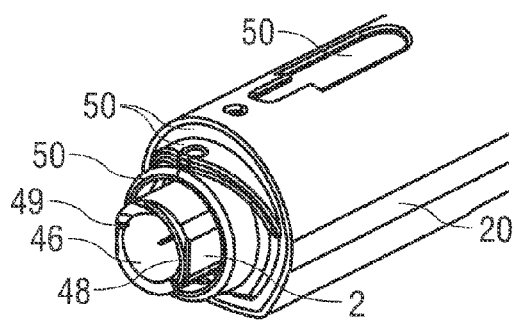
FIG. 6 is an isometric view of the proximal end of the auto-injector before removal of the cap.

After removal of the protective needle shield 36 the needle 4 is no longer protected but still a small distance back in the orifice 46. However, the orifice 46 would be wide enough to allow a user, at least a child to touch it with their fingers. In order to prevent finger access a spring wire 48 is arranged at the orifice 46. The spring wire 48 is attached to the chassis 2 and comprises an arcuate transversal section 48.1 biased in a manner to flex inwards so as to essentially obstruct the orifice 46 for finger access even for very small fingers while staying just enough off-centre to allow the needle 4 to advance without touching the spring wire 48 (cf. FIGS. 7 and 8). A notch 49 is arranged in a proximal face of the chassis 2 near the orifice 46 in a manner to lock the transversal section 48.1 in that position so it cannot easily be pushed aside by a user's finger. As long as the cap 44 is attached to the proximal end P the inner cylinder 45 keeps the arcuate transversal section 48.1 from flexing inwards (cf. FIGS. 4 and 6). FIG. 6 shows the situation when the cap 44 is in place without showing the cap 44 itself. FIG. 4 shows the proximal end of the auto-injector 1 without the interlock sleeve 25 during removal of the cap 44.

The spring wire 48 allows the needle 4 to be as near as possible to the proximal end P prior to actuation thus reducing travel of the syringe 3 and the overall length of the auto-injector 1 but still preventing needle stick injuries.

In the illustrated embodiment the cap 44 is held on the proximal end P by two fourth resilient clips 47. It could likewise be attached to the auto-injector 1 by a screw connection.

After removal of the cap 44 and the protective needle shield 36 the proximal end P of the auto-injector 1 is pressed against an injection site, e.g. a patient's skin. Thereby the skin interlock sleeve 25 is translated from a proximal position into a distal position against the bias of the interlock spring 26. When the pressure against the injection site is maintained or increased the sleeve trigger button 20 starts translating in proximal direction P. Typically, the auto-injector 1 is arranged to require a higher force for the trigger button 20 to translate than for the interlock sleeve 25 thus providing a two stage operation with a step in the force felt by the user when pushing the auto-injector 1 against the skin. As the trigger button 20 translates with respect to the chassis 2 the bar 57 is also translated until the wedge 55 can flex into a recess 59 in the bar 57 thus releasing the resilient arm 54, the decoupling sleeve 38, the thrust collar 37 and the plunger 9 in a manner to allow the drive spring 8 to translate them in proximal direction P.

The drive spring 8 now pushes the thrust collar 37 in proximal direction P taking with it the decoupling sleeve 38, the plunger 9, the decoupling carrier 41, the syringe carrier 9 and the syringe 3 with the needle 4 while no load is exerted onto the stopper 6. The hollow needle 4 appears from the proximal end P and is inserted into the injection site, e.g. the patient's skin.

The forward movement continues until the syringe carrier 9 bottoms out at a second abutment 32 in the chassis 2. The travel from the initial position up to this point defines an injection depth, i.e. needle insertion depth.

At the same time the decoupling carrier 41, moving relative to the retraction sleeve 10, reaches an aperture 60 in the retraction sleeve 10. The second resilient clips 42 of the decoupling carrier 41 are no longer outwardly supported by the retraction sleeve 10. As the drive spring 8 keeps pushing the plunger 9 the second resilient clips 42 are pushed out of the detent 43 by ramps or rounded edges at the distal sides of the detent 43 and the second clips 42. The plunger 9, no longer coupled to the decoupling carrier 41 and the syringe 3, keeps advancing and starts pushing against the stopper 6 for expelling the medicament M from the syringe 3 and injecting it into or through the patient's skin.

As the thrust collar 37, the decoupling sleeve 38 and the first clips 39 travel in proximal direction P the first clip 39 slides along the surface created by the out of phase castellations of the moving shutters 61 and fixed shutter 62.

When the auto-injector 1 is taken away from the injection site during the injection or at the end of injection the interlock sleeve 25 translates in proximal direction P under load of the interlock spring 26. Since the trigger button 20 and the head part 50 have translated in proximal direction P when the auto-injector 1 was triggered, the first abutment 5 in the head part 50 limiting travel of the interlock sleeve 25 is further in proximal direction P than in the initial state. Hence, the interlock sleeve 25 translates in proximal direction P beyond its initial proximal position into a final proximal position in which the leg 51 is removed from between the two resilient third clips 52 on the proximal end of the refraction sleeve 10 thus allowing them to flex inwards due to their ramped engagement to the protrusions 53 in the chassis 2 and due to the drive spring 8 pushing against the thrust face 13 of the retraction sleeve 10. The retraction sleeve 10 is now decoupled from the chassis 2 so the drive spring 8 is no longer grounded at its distal end. The refraction sleeve 10 translates in distal direction D until a first shoulder 63 in the retraction sleeve 10 hits a second shoulder 64 on the syringe carrier 7 under load of the drive spring 8 thus bringing the moving shutters 61 in phase with the fixed shutter 62 and creating a number of consecutive gaps between the aligned castellations.

If the retraction sleeve 25 is released mid injection the injection continues until the first clip 39 meets the next gap between the aligned castellations in proximal direction P. The first clip 39 is flexed inwards into the gap due to its ramped engagement to the thrust collar 37. Consequently, the thrust collar 37 and the decoupling sleeve 38 decouple and the plunger 9 stops advancing. The thrust collar 37, still under the force of the drive spring 8 continues travelling until it hits a stop on the chassis (not illustrated) giving the drive spring 8 a new ground at its proximal end. The retraction sleeve 10, still under the opposite force of the drive spring 8 and pushing with its first shoulder 63 against the second shoulder 64 of the syringe carrier 7 can now drag the whole assembly of syringe carrier 7, syringe 3, plunger 9 and decoupling sleeve 38 into the auto-injector 1 in distal direction D. The needle 4 is now a safe distance back in the auto-injector 1 thus preventing post injection needle stick injuries.

If the retraction sleeve 25 is released at the end of injection the first clip 39 has already travelled until the most proximal castellation of the moving shutter 61 which is now removed thus allowing the first clip 39 to flex inwards proximally from the aligned shutters 61, 62. The thrust collar 37 and the decoupling sleeve 38 decouple. The thrust collar 37, still under the force of the drive spring 8 continues travelling a short distance until it hits a stop on the chassis (not illustrated) giving the drive spring 8 a new ground at its proximal end and allowing the first clip 39 to dive through under the thrust collar 37 so the first clip 39 is not prevented from translating in distal direction D by the castellations. The refraction sleeve 10 under the opposite force of the drive spring 8 can now drag the whole assembly of syringe carrier 7, syringe 3, needle 4, plunger 9 and decoupling sleeve 38 into the auto-injector 1 in distal direction D. The needle 4 is now a safe distance back in the auto-injector 1 thus preventing post injection needle stick injuries.

The spring wire 48 serving as a finger guard may be applied with any auto-injector or other injection device.

The fixed shutter 62 and the moving shutter 61 form one embodiment of a shuttering mechanism for controlling translation of the plunger 9 relative to the chassis 2.

FIGS. 9 to 22 illustrate alternative embodiments of shuttering mechanisms.

Figure 9:
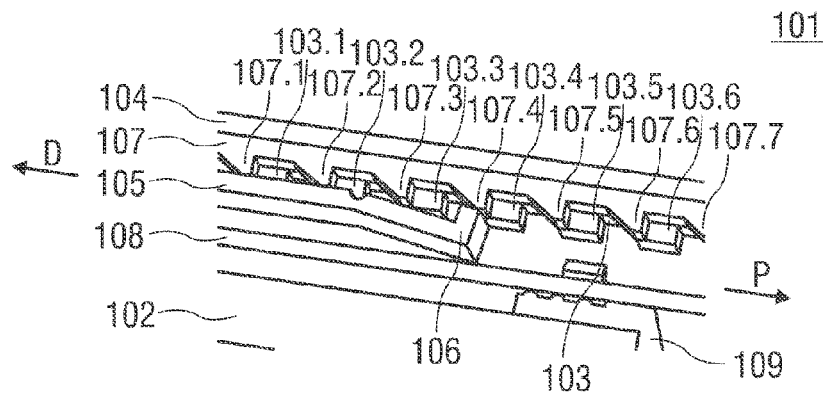
FIG. 9 is a detail view of a first alternative embodiment of a shuttering mechanism in an auto-injector.

FIG. 9 shows a shuttering mechanism 101 for controlling translation of a longitudinally moveable component 102. The shuttering mechanism 101 comprises at least one fixed shutter 103 having a set of fixed protrusions 103.1 to 103.6 in the shape of castellations 103.1 to 103.6, the fixed shutter 103 preferably being part of a housing 104 or chassis. The shuttering mechanism 101 furthermore comprises at least one resilient arm 105 associated with the longitudinally moveable component 102. At a proximal tip of the resilient arm 105 a dog 106 is resiliently biased towards the castellations 103.1 to 103.6 so as to engage between or behind the castellations 103.1 to 103.6 and block the translation of the longitudinally moveable component 102. A respective moving shutter arm 107 is arranged alongside the fixed shutter 103, the moving shutter arm 107 having a number of consecutive ramped moving protrusions 107.1 to 107.6 spaced from each other, their ramps facing in distal direction D. The castellations 103.1 to 103.6 and the ramped protrusions 107.1 to 107.6 have the same pitch and form a profiled surface. The moving shutter arm 107 is moveable in longitudinal direction with respect to the fixed shutter 103. The moving shutter arm 107 has at least one locking position with its ramped protrusions 107.1 to 107.6 essentially in phase with the castellations 103.1 to 103.6 thus allowing the dog 106 of the resilient arm 105 to catch between or behind the castellations 103.1 to 103.6. The moving shutter arm 107 has at least one unlocking position with its ramped protrusions 107.1 to 107.6 out of phase with the castellations 103.1 to 103.6 in such a manner that the ramped protrusions 107.1 to 107.6 prevent the dog 106 from engaging with the castellations 103.1 to 103.6 or disengage them thus allowing translation of the longitudinally moveable component 102.

The longitudinally moveable component 102 is preferably a plunger 102 for transmitting a driving force of a drive means, e.g. a spring to a syringe 108 or to a stopper 109 for sealing the syringe 108 and displacing a liquid medicament from the syringe 108. The syringe 108, the shuttering mechanism 101, the plunger 102 and the drive means may be part of an auto-injector for delivering the medicament.

FIG. 9 shows the shuttering mechanism 101 during an injection.

Prior to use the plunger 102 resolves the driving force acting in proximal direction P into the fixed shutter 103. The moving shutter arm 107 is in phase with the fixed shutter 103 and hence carries no load. The plunger 102 cannot be pushed in proximal direction P because of the dog 106 caught behind the most distal castellation 103.1.

To allow translation of the plunger 102 in proximal direction P, the moving shutter arm 107 must be translated in distal direction D relative to the fixed shutter 103, such that they are out of phase. The ramp of the most distal moving protrusion 107.1 of the moving shutter arm 107 cams the dog 106 out of engagement with the fixed shutter 103, to the same level as the top of the first castellation 103.1. At this point the plunger 102 is free to move in proximal direction P under the driving force. If the relative position of the shutters 103, 107 is held constant, the dog 106 will continue to ride up the surface formed by the out of phase fixed shutter 103 and moving shutter arm 107 in proximal direction P as shown in FIG. 9.

Figure 10:
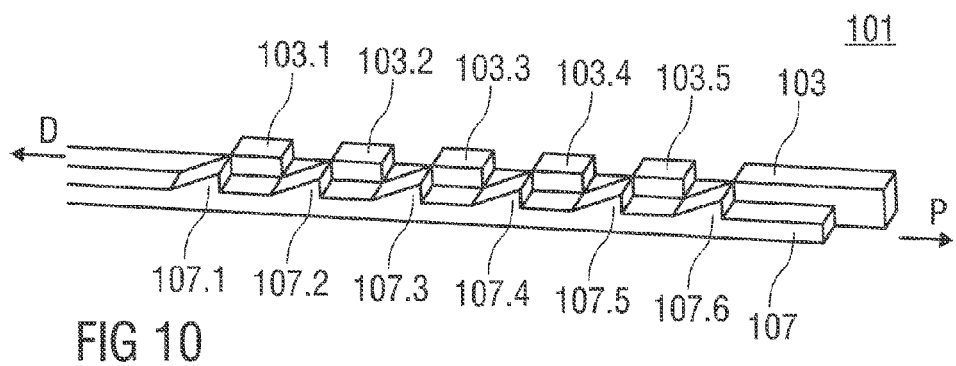
FIG. 10 is a schematic view of the shuttering mechanism of FIG. 9 with a moving shutter arm with ramped moving protrusions.

In the embodiment shown in FIGS. 9 and 10 the dog 106 running along the surface will produce a sound each time it snaps off the top of the fixed shutter 103 castellation 103.1 to 103.6 and will alternately apply a force to the moving shutter arm 107 as it rides up the ramps of the moving protrusions 107.1 to 107.6. This will provide both audible and tactile feedback that the injection is taking place. Once these stop, the injection is complete.

If the moving shutter arm 107 is translated back in phase with the fixed shutter 103 during the injection (either by moving it further in distal direction D, or moving it towards the position it was prior to firing), the dog 106 will catch on the next fixed shutter 103 castellation 103.1 to 103.6 and stop the injection. The injection can then be restarted by translating the moving shutter arm 107 in phase with the fixed shutter 103 again. Alternatively the moving shutter arm 107 may be latched or disconnected from the user's control, preventing any further dose from being delivered.

Figure 11:
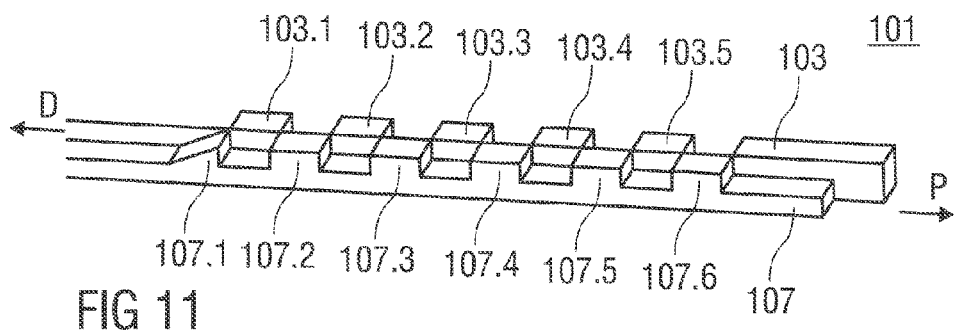
FIG. 11 is a schematic view of a second alternative embodiment of the shuttering mechanism.

FIG. 11 shows an alternative embodiment of the shuttering mechanism 101. The moving shutter arm 107 has only one ramped moving protrusion 107.1 while the other moving protrusions 107.2 to 107.6 are castellations. If the moving shutter arm 107 is translated in phase with the fixed shutter 103 during translation of the plunger 102, the dog 106 will flex into the next space between the castellations 103.1 to 103.5, 107.1 to 107.6 and remain there since it cannot be ramped out by the moving shutter arm 107, again. Hence, the injection, once stopped cannot be restarted. The embodiment of FIG. 11 does not produce an audible or tactile feedback during the translation of the plunger 102, e.g. during injection.

Figure 12:
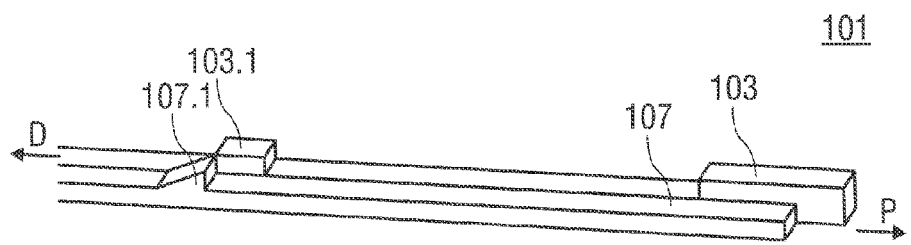
FIG. 12 is a schematic view of a third alternative embodiment of the shuttering mechanism.

FIG. 12 shows another embodiment of the shuttering mechanism 101 wherein only one fixed castellation 103.1 is provided on the fixed shutter 103 and only one ramped moving protrusion 107.1 on the moving shutter arm 107. To allow translation of the plunger 102 in proximal direction P, the moving shutter arm 107 must be translated in distal direction D relative to the fixed shutter 103, such that they are out of phase as in FIG. 12. The ramp of the moving protrusion 107.1 cams the dog 106 out of engagement with the fixed shutter 103, to the same level as the top of the fixed castellation 103.1. At this point the plunger 102 is free to move in proximal direction P under the driving force. From this point on the injection continues without the user being able to pause or stop it. The embodiment of FIG. 12 does not produce an audible or tactile feedback during the translation of the plunger 102, e.g. during injection.

Figure 13:
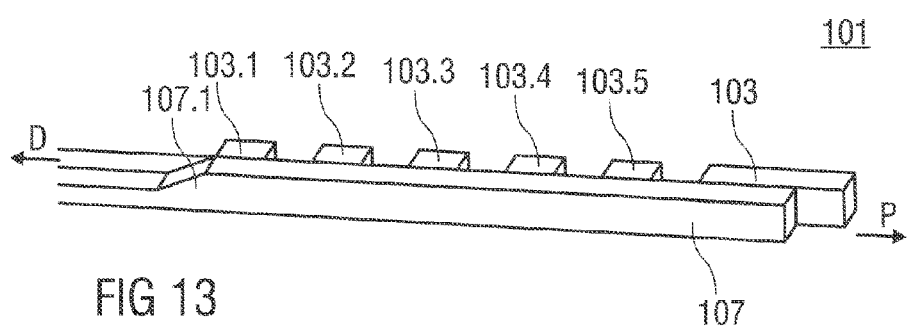
FIG. 13 is a schematic view of a fourth alternative embodiment of the shuttering mechanism.

FIG. 13 is an embodiment of the shuttering mechanism wherein a set of castellations 103.1 to 103.5 is provided on the fixed shutter 103 and only one ramp 107.1 on the moving shutter arm 107. Proximally from that ramp 107.1 the moving shutter arm 107 remains on the top level of the ramp 107.1. To allow translation of the plunger 102 in proximal direction P, the moving shutter arm 107 must be translated in distal direction D relative to the fixed shutter 103, such that they are out of phase as in FIG. 13. The ramp 107.1 of the moving shutter arm 107 cams the dog 106 out of engagement with the fixed shutter 103, to the same level as the top of the castellation 103.1. At this point the plunger 102 is free to move in proximal direction P under the driving force. From this point on the injection continues without the user being able to pause or stop it. The embodiment of FIG. 13 does not produce an audible or tactile feedback during the translation of the plunger 102, e.g. during injection. This embodiment allows for using the same housing 104 with the integrated fixed shutter 103 as in the embodiment of FIGS. 9 and 10. The functionality is changed just by applying the modified moving shutter arm 107. This allows for creating a platform of auto-injectors with a number of common parts, where only some parts have to be exchanged in order to change the functionality.

Figure 14:
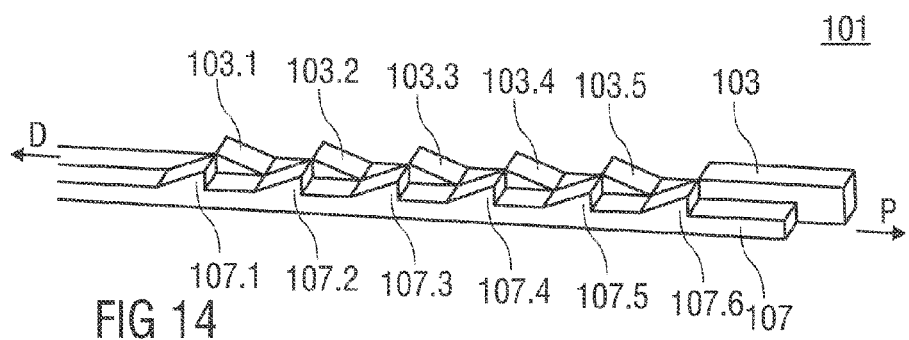
FIG. 14 is a schematic view of a fifth alternative embodiment of the shuttering mechanism.

FIG. 14 is yet another embodiment of the shuttering mechanism 101. The shuttering mechanism 101 comprises at least one fixed shutter 103 in the shape of a set of ramped moving protrusions 103.1 to 103.5. The ramps of the ramped fixed protrusions 103.1 to 103.5 of the fixed shutter 103 face in proximal direction P. A respective moving shutter arm 107 is arranged alongside the fixed shutter 103, the moving shutter arm 107 having a number of consecutive ramped fixed protrusions 107.1 to 107.6 spaced from each other, their ramps facing in distal direction D. The ramped fixed protrusions 103.1 to 103.5 of the fixed shutter 103 and the ramped moving protrusions 107.1 to 107.6 of the moving shutter arm 107 have the same pitch and form a profiled surface. The moving shutter arm 107 is moveable in longitudinal direction with respect to the fixed shutter 103. The moving shutter arm 107 has at least one locking position with its ramped moving protrusions 107.1 to 107.6 essentially in phase with the ramped fixed protrusions 103.1 to 103.5 of the fixed shutter 103 thus allowing the dog 106 of the resilient arm 105 to catch between or behind the ramped fixed protrusions 103.1 to 103.5 of the fixed shutter 103. The moving shutter arm 107 has at least one unlocking position with its ramped moving protrusions 107.1 to 107.6 out of phase with the ramped fixed protrusions 103.1 to 103.5 in such a manner that the ramped moving protrusions 107.1 to 107.6 prevent the dog 106 from engaging with the ramped fixed protrusions 103.1 to 103.5 or disengage them thus allowing translation of the longitudinally moveable component 102.

Prior to use the plunger 102 resolves the driving force acting in proximal direction P into the fixed shutter 103. The moving shutter arm 107 is in phase with the fixed shutter 103 and hence carries no load. The plunger 102 cannot be pushed in proximal direction P because of the dog 106 caught behind the most distal ramped fixed protrusion 103.1 of the fixed shutter 103.

To allow translation of the plunger 102 in proximal direction P, the moving shutter arm 107 must be translated in distal direction D relative to the fixed shutter 103, such that they are out of phase. The ramp of the most distal ramped fixed protrusion 107.1 of the moving shutter arm 107 cams the dog 106 out of engagement with the fixed shutter 103, to the same level as the top of the ramped fixed protrusion 103.1. At this point the plunger 102 is free to move in proximal direction P under the driving force. If the relative position of the shutters 103, 107 is held constant, the dog 106 will continue to ride up and down the surface formed by the out of phase fixed shutter 103 and moving shutter arm 107.

Figure 15:
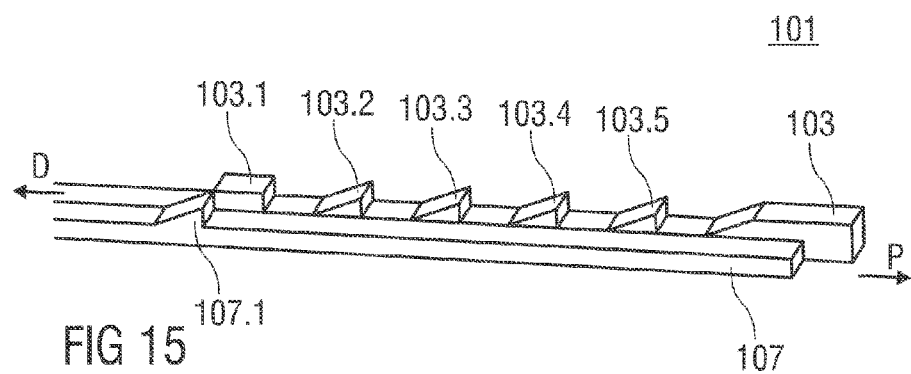
FIG. 15 is a schematic view of a sixth alternative embodiment of the shuttering mechanism.

In the embodiment shown in FIG. 15 the dog 106 running along the surface will provide both audible and tactile feedback that the injection is taking place, but muffled in comparison to the embodiment of FIG. 9.

As in the embodiment of FIG. 9 the injection can be interrupted and restarted. Furthermore, the ramped fixed protrusions 103.1 to 103.5 of the fixed shutter 103 in place of the castellations allow for implementing a retraction of the plunger 102 and consequently retraction of the syringe 108 and needle, since as the fixed shutter 103 and the moving shutter arm 107 are out of phase as in FIG. 14, the dog 106 can run in distal direction D as well without catching between the ramped protrusions 103.1 to 103.5, 107.1 to 107.6 of either shutter 103, 107.

FIG. 15 is another embodiment of the shuttering mechanism 101. The shuttering mechanism 101 comprises at least one fixed shutter 103 with a set of fixed protrusions 103.1 to 103.5, the most distal one of them in the shape of a castellation 103.1 and the other protrusions 103.2 to 103.5 ramped with their ramps facing in distal direction D. A moving shutter arm 107 is arranged alongside the fixed shutter 103, the moving shutter arm 107 having one ramped protrusion 107.1 with its ramp facing in distal direction D. The moving shutter arm 107 is moveable in longitudinal direction with respect to the fixed shutter 103.

Prior to use the plunger 102 resolves the driving force acting in proximal direction P into the fixed castellation 103.1 of the fixed shutter 103. The ramped moving protrusion 107.1 of the moving shutter arm 107 is in phase with the fixed castellation 103.1 of the fixed shutter 103. The plunger 102 cannot be pushed in proximal direction P because of dog 106 caught behind the fixed castellation 103.1 of the fixed shutter 103.

To allow translation of the plunger 102 in proximal direction P, the moving shutter arm 107 must be translated in distal direction D relative to the fixed shutter 103, such that they are out of phase. The ramp of the ramped moving protrusion 107.1 cams the dog 106 out of engagement with the fixed shutter 103, to the same level as the top of the first fixed protrusion 103.1. At this point the plunger 102 is free to move in proximal direction P under the driving force. From this point on the injection continues without the user being able to pause or stop it. The dog 106 will continue to ride up and down the surface formed by the fixed protrusions 103.2 to 103.5.

In the embodiment shown in FIG. 15 the dog 106 running along the surface will provide only an audible feedback that the injection is taking place. If the moving shutter 107 had ramped protrusions 107.2 to 107.6 and the fixed shutter 103 had none, the shuttering mechanism 101 could also provide a tactile feedback.

Figure 16A:
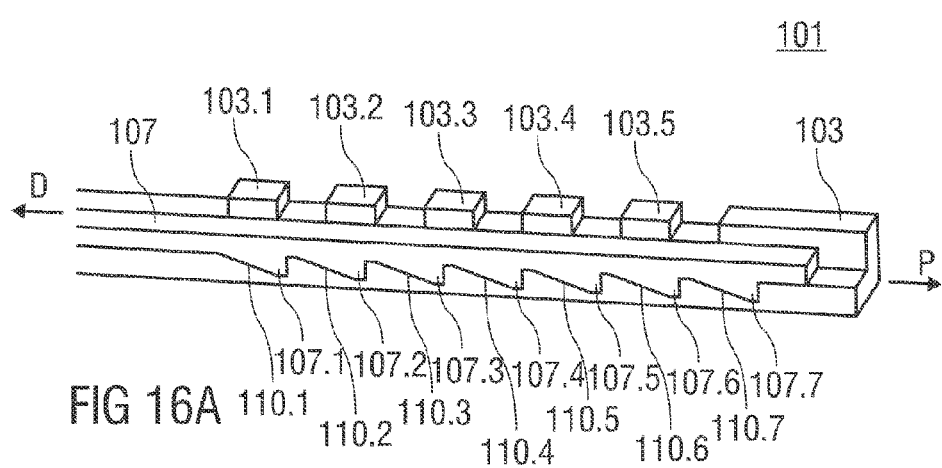
FIG. 16a is a schematic view of a seventh alternative embodiment of the shuttering mechanism prior to actuation.
Figure 16B:
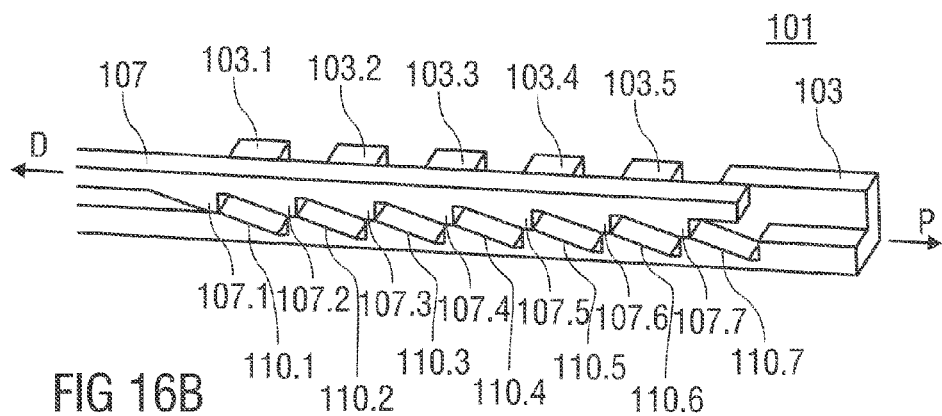
FIG. 16b is a schematic view of the seventh alternative embodiment of the shuttering mechanism during translation.

FIGS. 16a and 16b show yet another embodiment of the shuttering mechanism 101.

The shuttering mechanism 101 comprises at least one fixed shutter 103 with a set of fixed protrusions 103.1 to 103.5 in the shape of castellations protruding to one side. A moving shutter arm 107 is arranged alongside the fixed shutter 103, the moving shutter arm 107 having ramped moving protrusions 107.1 to 107.7 protruding to the opposite side with their ramps facing in distal direction D and engaged with mating ramps 110.1 to 110.7 in the fixed shutter 103. The moving shutter arm 107 is moveable in longitudinal direction with respect to the fixed shutter 103.

Prior to use (see FIG. 16a) the plunger 102 resolves the driving force acting in proximal direction P into the fixed castellation 103.1 of the fixed shutter 103. The ramped moving protrusions 107.1 to 107.7 of the moving shutter arm 107 are fully engaged with the mating ramps 110.1 to 110.7 of the fixed shutter 103. The plunger 102 cannot be pushed in proximal direction P because of dog 106 caught behind the fixed castellation 103.1 of the fixed shutter 103.

To allow translation of the plunger 102 in proximal direction P, the moving shutter arm 107 must be translated in distal direction D relative to the fixed shutter 103. The engaged ramped moving protrusions 107.1 to 107.7 and the mating ramps 110.1 to 110.7 push the moving shutter arm 107 away from the fixed shutter 103 so that a backside of the moving shutter arm 107 opposite the protrusions 107.1 to 107.7 becomes flush with the top of the fixed protrusions 103.1 to 103.5 thus disengaging the dog 106 from the fixed shutter 103 (see FIG. 16b). At this point the plunger 102 is free to move in proximal direction P under the driving force. If the relative position of the shutters 103, 107 is held constant, the dog 106 will continue to ride up the surface formed by the fixed shutter 103 and moving shutter arm 107 in proximal direction P.

If the moving shutter arm 107 is translated back in proximal direction P, the moving shutter 107 is no longer forced away from the fixed shutter 103 and the ramped moving protrusions 107.1 to 107.7 and the mating ramps 110.1 to 110.7 fully re-engage. The dog 106 will catch on the next fixed shutter 103 castellation 103.1 to 103.6 and stop the injection. The injection can then be restarted by translating the moving shutter arm 107 in distal direction D again.

In the embodiment of FIGS. 16a and 16b the number of moving protrusions 107.1 to 107.7 and their pitch relative to the pitch of the fixed protrusions 103.1 to 103.5 is insignificant other than to define the amount of distal movement of moving shutter arm 107 required to start or stop the proximal movement of plunger 102. It would be sufficient to have one moving protrusion 107.1 and one mating ramp 110.1. However, at least two moving protrusions 107.1 to 107.7 and two mating ramps 110.1 to 110.7 will be more robust.

The embodiment of FIGS. 16a and 16b does not provide audio or tactile feedback. Because there is no requirement for phasing between the fixed shutter 103 and the moving shutter 107, the fixed protrusions 103.1 to 103.5 can be thin and close together resulting in a better resolution of stopping positions. Other than in the previously described embodiments, where the distance between the fixed protrusions 103.1 to 103.5 is driven by the length of the ramps, which is driven by the force/displacement specified to release the dog 106, in the embodiment of FIGS. 16a and 16b the ramps of the moving protrusions 107.1 to 107.7 are independent of the fixed protrusions 103.1 to 103.5. Hence, more, closely spaced fixed protrusions 103.1 to 103.n can be used for improving the resolution of stopping positions.

Figure 17:
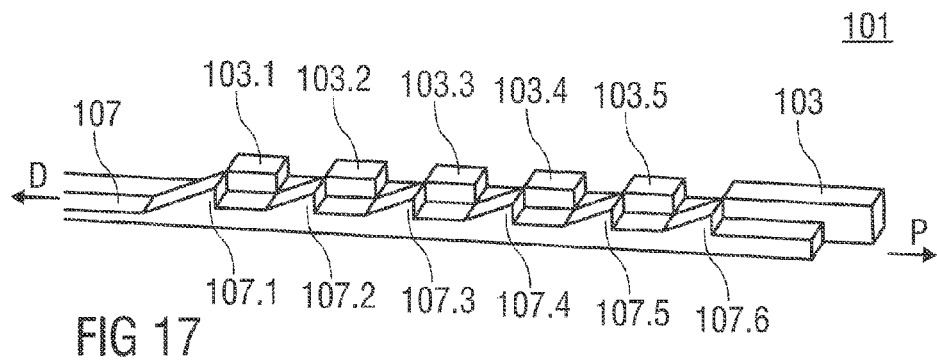
FIG. 17 is a schematic view of an eighth alternative embodiment of the shuttering mechanism.
Figure 18:
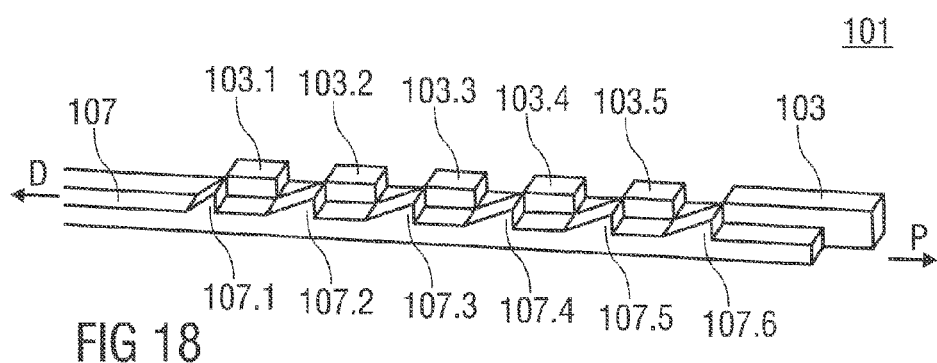
FIG. 18 is a schematic view of a ninth alternative embodiment of the shuttering mechanism.
Figure 19:
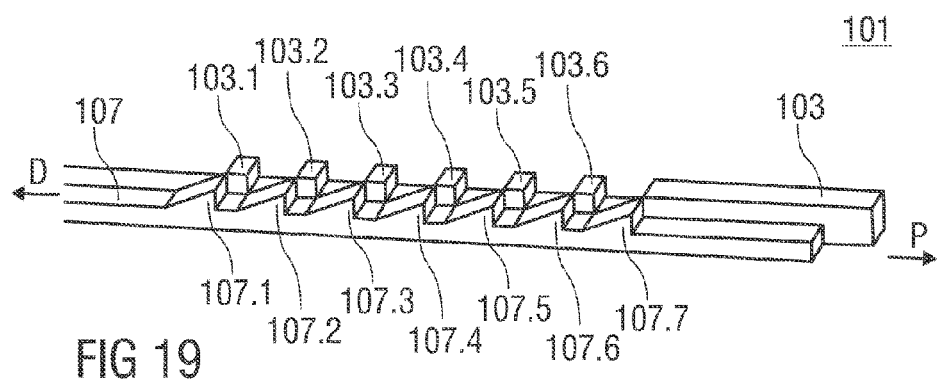
FIG. 19 is a schematic view of a tenth alternative embodiment of the shuttering mechanism.
Figure 20A:
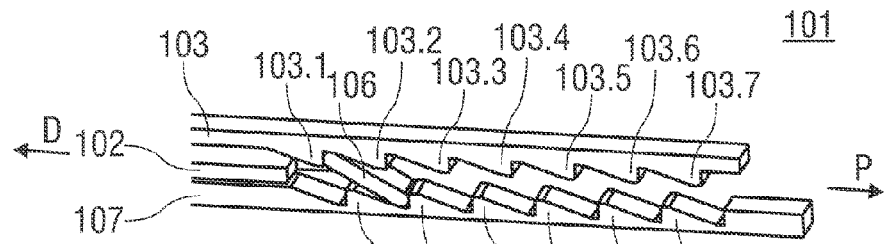
FIG. 20 is a schematic view of an eleventh alternative embodiment of the shuttering mechanism.
Figure 20B:
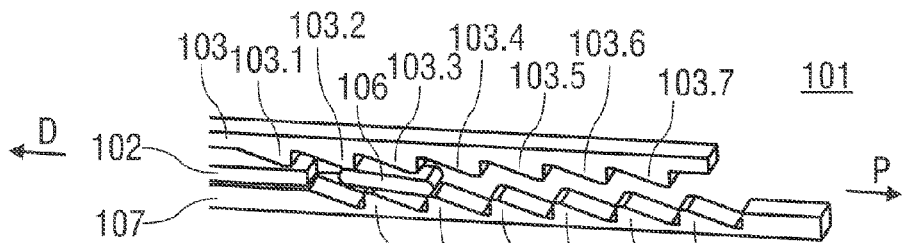
Figure 20C:
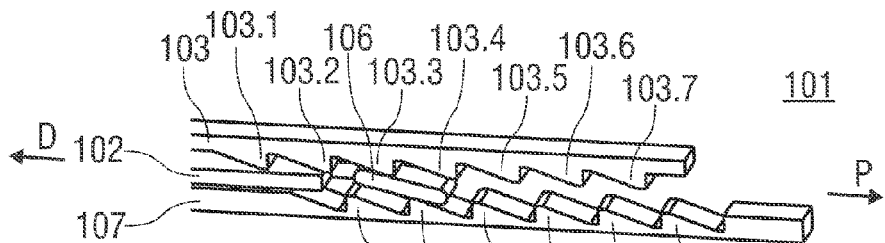
Figure 20D:
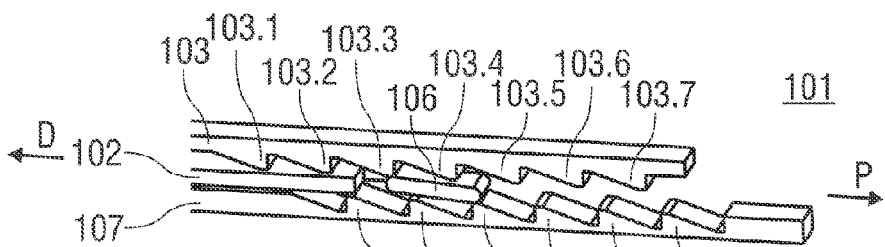

FIGS. 17, 18 and 19 show variants of the embodiment of FIGS. 9 and 10.

In FIG. 17, the level of the moving shutter arm 107 distally from the most distal ramped moving protrusion 107.1 as well as the level of the fixed shutter 103 distally from the most distal fixed protrusion 103.1 is below the level between the protrusions 103.1 to 103.5, 107.1 to 107.6. Consequently, the ramp of the ramped moving protrusion 107.1 is longer and camming the dog 106 from its position prior to use (distally from the protrusions 103.1, 107.1) requires more travel of the moving shutter 107 than for restarting the injection. This reduces the sensitivity of the arrangement to initial movement of the moving shutter arm 107, thereby reducing the chance of accidental triggering at the start of injection, yet maintains the ability to stop quickly. A good resolution between stopping points is provided.

In FIG. 18, the ramp of the most distal ramped moving protrusion 107.1 is steeper than the ramps of the other ramped moving protrusions 107.2 to 107.6. Consequently, camming the dog 106 from its position prior to use (distally from the protrusions 103.1, 107.1) requires more increased force on the moving shutter 107 than for restarting the injection. This reduces the chance of unintended triggering at the start of injection.

In the embodiments which allow stopping and/restarting the injection, there will always be an amount of liquid medicament dispensed before the injection actually stops since the dog 106 has to travel until the distal edge of the next fixed protrusion 103.1 to 103.5. In order to reduce this amount of medicament the auto-injector may have at least two shuttering mechanisms 101 (e.g. one on either side of the auto-injector) which are out of phase with each other. Thus, the effective pitch of the shutter mechanism 101 would be halved and the dispensed dose of medicament until the stop would be significantly reduced.

In FIG. 19, the fixed protrusions 103.1 to 103.6 and the moving protrusions 107.1 to 107.7 have different length. In order to control translation of the plunger 102 it is sufficient to cover the proximal edge of the moving protrusions 107.1 to 107.7 by the fixed protrusions 103.1 to 103.6. Complete overlap is not required. This allows the pitch of the shutters to be reduced so less medicament will be dispensed when the injection is interrupted. In this arrangement, the width of dog 106 in the axial direction needs to be sufficiently short that it will engage between the proximal edge of moving protrusion 107.1 to 107.7 and the distal edge of fixed protrusion 103.1 to 103.6 when the moving shutter arm 107 is moved out of phase with the fixed shutter 103.

The shuttering mechanism 101 may likewise be applied in other environments requiring control of translation of a longitudinally moveable component 102 other than a plunger 102.

The numbers of fixed protrusions 103.1 to 103.6 and moving protrusions 107.1 to 107.7 can differ from the numbers given in the embodiments.

Preferably, motion of the moving shutter arm 107 can be actuated by pressing a proximal end of an auto-injector against an injection site, e.g. a user's skin thereby pushing a sleeve or bar protruding from the proximal end of the auto-injector in distal direction. The motion may likewise be actuated by pushing an end button or indirectly through a cam or other mechanism linked to a side button or end button.

In addition, the auto-injector could be triggered by a secondary mechanism and the shuttering mechanism 101 could simply be used as a control mechanism. In this implementation, the moving shutter's 107 position would be controlled by a 'pause' button. This would separate the mechanisms to fire and pause the auto-injector, improving usability.

The 'pause' button could be designed to be 'press to inject' or 'press to pause'. The trigger could be combined with the pause button if the mechanism were 'press to inject'.

In an alternative embodiment the moving shutter 107 may be arranged to rotate or translate in the direction perpendicular to the shutters into the gaps between the fixed protrusions 103.1 to 103.5 rather than translated longitudinally as in the illustrated embodiments.

In yet another alternative embodiment, shown in FIG. 20, the shutters 103, 107 could be facing each other and the plunger 102 could navigate a gap created between the shutters 103, 107. For this arrangement, the distal faces of the fixed protrusions 103.1 to 103.5 and moving protrusions 107.1 to 107.6 both need to be ramped in order to allow the dog 106 to pass along the passage formed when the protrusions are moved out of phase.

Figure 21A:
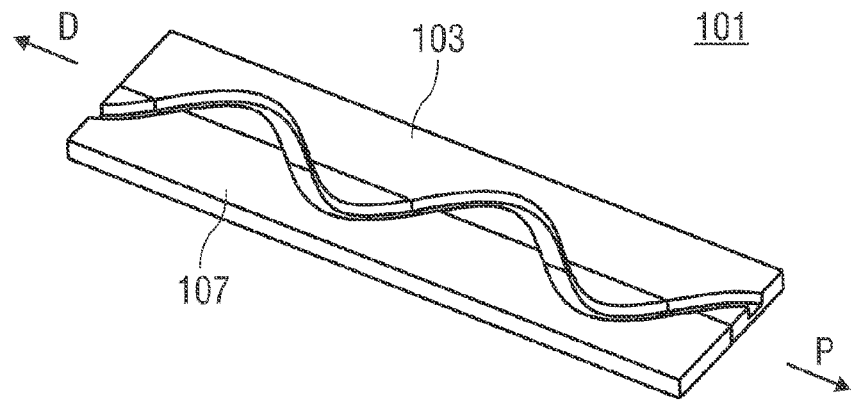
FIG. 21 is a schematic view of a twelfth alternative embodiment of the shuttering mechanism.
Figure 21B:
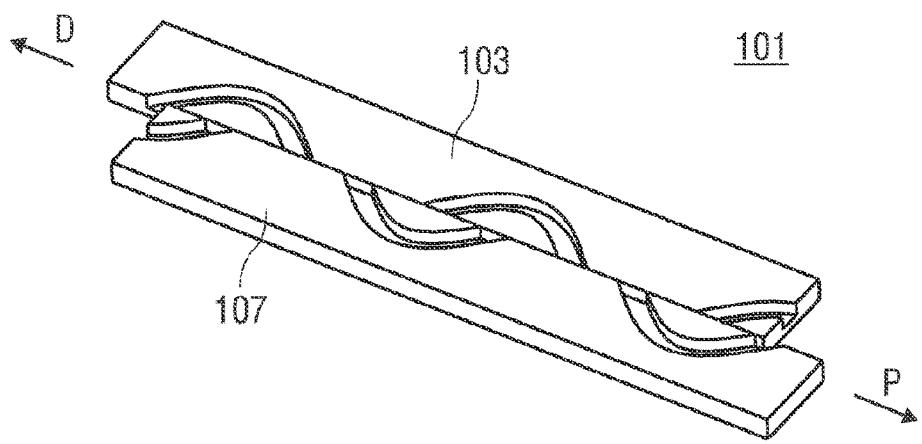
Figure 22A:
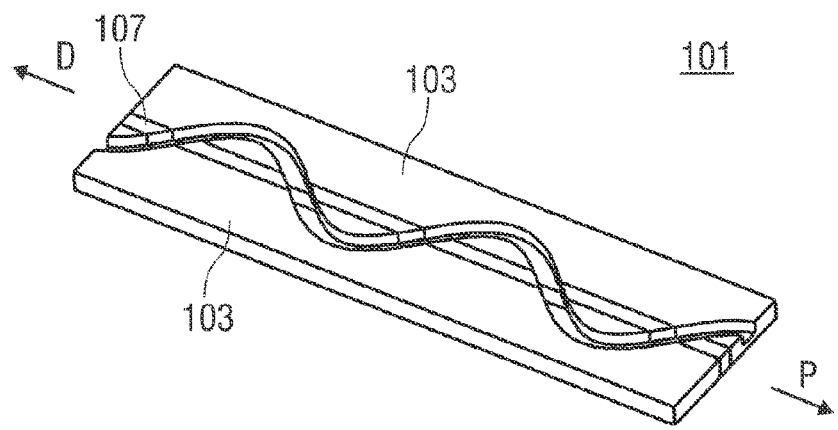
FIG. 22 is a schematic view of thirteenth alternative embodiment of the shuttering mechanism.
Figure 22B:
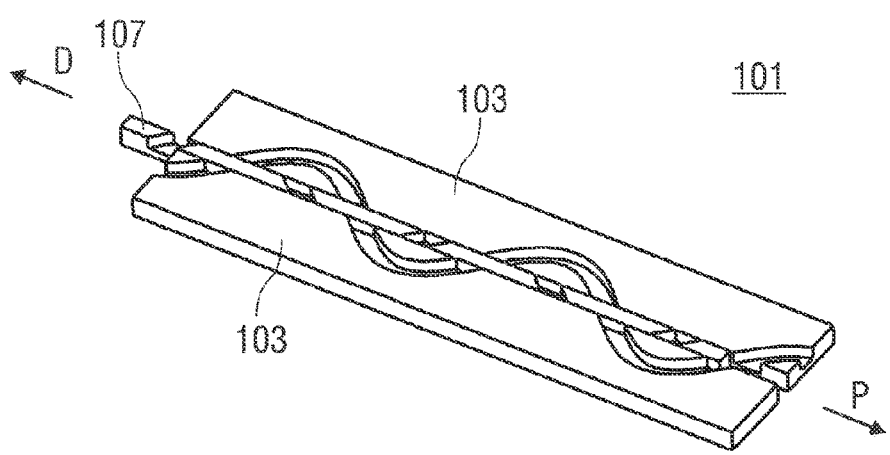

In yet another embodiment the dog 106 could oscillate through a continuous sinusoidal path cut into the two shutters 103, 107 (see FIGS. 21 and 22). The sinusoidal path would be broken by shifting the moving shutter 107 into the locking position thus preventing the dog 106 from advancing beyond the next change-over between the shutters 103, 107.

The invention claimed is:

1. A finger guard for an injection device with a hollow injection needle arranged to be hidden inside a component with an orifice prior to use and to be advanced relative to the component through the orifice for inserting it into an injection site, a notch is arranged in a proximal most face of the component formed on a proximal end of the component near the orifice, the finger guard comprising a spring wire attached to the component and comprising an arcuate transversal section biased in a manner to flex inwards cantilevering into the orifice so as to essentially obstruct the orifice for finger access when released but staying enough off-center to allow the needle to advance through the orifice without touching the spring wire, wherein the notch locks the arcuate transversal section.

2. The finger guard according to claim 1, wherein the arcuate transversal section is arranged to catch in the notch when allowed to flex inwards.

3. The finger guard according to claim 1, characterized in that a cap is arrangeable at the component, the cap comprising an inner cylinder arranged to extend into the orifice, wherein the inner cylinder is arranged for keeping the arcuate transversal section from flexing inwards when attached to the component.

4. The finger guard according to claim 1, characterized in that the component is arranged as a chassis of the injection device.

5. The finger guard according to claim 1, characterized in that the component is arranged as a tubular shroud arranged to be advanced for covering the needle and to be retracted for exposing the needle.

6. An auto-injector for administering a dose of a liquid medicament with a finger guard according to claim 4, wherein the chassis is arranged to contain a syringe with the needle and a stopper for sealing the syringe and displacing the dose of liquid medicament, wherein the syringe is slidably arranged with respect to the chassis, the auto-injector furthermore comprising:
a driver capable of, upon activation:
pushing the needle from a covered position inside the chassis into an advanced position through the orifice,
operating the syringe to supply the dose of liquid medicament, and
retracting the syringe with the needle into the covered position after delivering the dose of liquid medicament; and
an activating mechanism arranged to lock the driver prior to manual operation and capable of, upon manual operation, releasing a drive spring for injection.

7. The auto-injector according to claim 6, characterized in that the driver is a drive spring in the shape of a compression spring arranged to be grounded at a distal end in the chassis for advancing the needle and for injecting the dose of liquid medicament via a plunger, wherein the drive spring is arranged to have its ground in the chassis switched to its proximal end for retracting the syringe.

8. The auto-injector according to claim 7, characterized in that a retraction sleeve is axially movable arranged around the syringe, wherein the retraction sleeve is fixable to the chassis in a maximum proximal position for providing ground at the distal end of the drive spring, wherein the retraction sleeve is arranged to take the syringe with it when released and translated in a distal direction, wherein the drive spring is wrapped over the retraction sleeve with its distal end bearing against a thrust face on the retraction sleeve and with its proximal end bearing against a thrust collar arranged to be coupled to the plunger for joint axial translation for advancing the needle and for injecting the dose of liquid medicament and wherein the thrust collar is arranged to be decoupled from the plunger for retraction.

9. The auto-injector according to claim 8, characterized in that the activating mechanism is arranged as a trigger button in the shape of a wrap-over sleeve button arranged over the distal end of the auto-injector, the trigger button extending at least almost over a whole length of the auto-injector, wherein the trigger button is arranged to release the drive spring upon translation in proximal direction.

10. The auto-injector according to claim 9, characterized in that an interlock sleeve is telescoped with the proximal end of the chassis and with the trigger button, the interlock sleeve translatable in a longitudinal direction between a proximal position relative to the trigger button and a distal position relative to the chassis and biased towards the proximal position, wherein the interlock sleeve is arranged to release the retraction sleeve when in the proximal position and with the trigger button translated in the proximal direction and wherein the interlock sleeve is arranged to block the translation of the retraction sleeve otherwise.

11. The auto-injector according to claim 10, characterized in that the interlock sleeve comprises at least one leg arranged distally, wherein at least one resilient clip is arranged on the proximal end of the retraction sleeve, wherein a respective protrusion for each at least one resilient clip is arranged on the chassis, wherein the at least one resilient clip or the respective protrusion exhibits a ramp for flexing the at least one resilient clip away from the respective protrusion thus disengaging the at least one resilient clip from the respective protrusion under load of the drive spring thus releasing the retraction sleeve, wherein the at least one leg is arranged to allow this disengagement when the interlock sleeve is in the proximal position with the trigger button translated in the proximal direction, wherein otherwise the at least one leg is arranged to support the at least one resilient clip in a manner to prevent it from flexing away from the respective protrusion thus keeping them engaged and blocking the retraction sleeve.

12. The auto-injector according to claim 8, characterized in that the refraction sleeve exhibits at least one moving shutter and the chassis comprises a fixed shutter, wherein the moving shutter and the fixed shutter respectively comprise a number of regularly spaced castellations, wherein the castellations of the moving shutter are out of phase with the castellations of the fixed shutter when the retraction sleeve is fixed in the maximum proximal position thus creating a surface of alternating castellations of both shutters for a respective first clip to travel along, wherein the first clip is arranged to keep the thrust collar coupled to the plunger when on the surface of alternating castellations, wherein on translation of the retraction sleeve the moving shutter gets in phase with the fixed shutter in a manner to regularly interupt the surface of alternating castellations by gaps allowing the first clip to be flexed inwards by at least one ramp on the first clip and/or the thrust collar under load of the drive spring thus decoupling the thrust collar from the plunger.

13. The auto-injector according to claim 8, characterized in that a decoupling sleeve is arranged around the retraction sleeve inside the drive spring and attached to the plunger at a distal end, wherein prior to manual operation of the activating mechanism the thrust collar is coupled through the first clip and the decoupling sleeve to the refraction sleeve, wherein the activating mechanism is arranged to prevent decoupling of the decoupling sleeve from the retraction sleeve prior to actuation and to allow decoupling on actuation.

14. The auto-injector according to claim 13, characterized in that the decoupling sleeve exhibits a resilient arm protruding in the distal direction, the resilient arm having a wedge arranged to be held between a ramp on the retraction sleeve and a bar protruding in a proximal direction from a distal end face of the trigger button prior to actuation of the trigger button, wherein upon actuation of the trigger button the bar is translated so as to allow the wedge to be flexed into a recess in the bar by the ramp under load of the drive spring.

15. The auto-injector according to claim 8, characterized in that a decoupling carrier is slidably arranged in the retraction sleeve and coupled to the syringe for joint axial translation, wherein the decoupling carrier comprises at least one resilient clip engageable in a detent in the plunger in a manner to lock the decoupling carrier to the plunger for joint axial translation, wherein the retraction sleeve is arranged for outwardly supporting the at least one resilient clip prior to the syringe reaching an injection depth during needle insertion, wherein a respective aperture is arranged in the retraction sleeve allowing the at least one resilient clip to be flexed outwards and disengage from the detent upon the syringe reaching the injection depth thus coupling the plunger to the stopper.

\* \* \* \* \*